United States Patent
Masuda et al.

(10) Patent No.: US 8,840,910 B2
(45) Date of Patent: Sep. 23, 2014

(54) ANTIFOULING COATING COMPOSITION AND USES OF THE SAME

(75) Inventors: Satoshi Masuda, Otake (JP); Yusuke Hayashi, Otake (JP); Yukio Kozono, Otake (JP)

(73) Assignee: Chugoku Marine Paints, Ltd., Otake-shi (JP)

( * ) Notice: Subject to any disclaimer, the term of this patent is extended or adjusted under 35 U.S.C. 154(b) by 0 days.

(21) Appl. No.: 13/636,013

(22) PCT Filed: Mar. 18, 2011

(86) PCT No.: PCT/JP2011/056571
§ 371 (c)(1),
(2), (4) Date: Oct. 22, 2012

(87) PCT Pub. No.: WO2011/118526
PCT Pub. Date: Sep. 29, 2011

(65) Prior Publication Data
US 2013/0045264 A1    Feb. 21, 2013

(30) Foreign Application Priority Data

Mar. 23, 2010  (JP) ................. 2010-065965

(51) Int. Cl.
| | | |
|---|---|---|
| A01N 25/08 | (2006.01) | |
| A01N 59/20 | (2006.01) | |
| A01N 55/02 | (2006.01) | |
| A01N 43/64 | (2006.01) | |
| A01N 43/80 | (2006.01) | |
| A01N 43/50 | (2006.01) | |
| C09D 133/02 | (2006.01) | |
| C09D 143/04 | (2006.01) | |
| C09D 5/16 | (2006.01) | |
| B63B 59/04 | (2006.01) | |
| C09D 167/00 | (2006.01) | |
| C08K 5/00 | (2006.01) | |
| C08K 3/00 | (2006.01) | |
| E02B 17/00 | (2006.01) | |

(52) U.S. Cl.
CPC .............. *B63B 59/04* (2013.01); *C09D 133/02* (2013.01); *C09D 143/04* (2013.01); *C09D 5/165* (2013.01); *A01N 43/50* (2013.01); *C09D 5/1625* (2013.01); *C09D 167/00* (2013.01); *C08K 5/0058* (2013.01); *C08K 3/005* (2013.01); *E02B 17/0017* (2013.01)
USPC ........... 424/409; 424/635; 424/637; 424/638; 514/188; 514/245; 514/372; 514/396

(58) Field of Classification Search
USPC .......... 424/409, 635, 637, 638; 514/188, 245, 514/372, 396, 64; 427/387
See application file for complete search history.

(56) References Cited

U.S. PATENT DOCUMENTS

| | | | |
|---|---|---|---|
| 6,458,878 B1 | 10/2002 | Tsuboi et al. | |
| 6,762,227 B1 * | 7/2004 | Elwing et al. | .................. 524/106 |
| 7,311,766 B2 * | 12/2007 | Nyden et al. | ................ 106/18.32 |
| 2006/0201379 A1 | 9/2006 | Nyden et al. | |
| 2006/0223906 A1 | 10/2006 | Nyden et al. | |
| 2007/0028825 A1 * | 2/2007 | Martensson | ................... 114/222 |

FOREIGN PATENT DOCUMENTS

| | | | |
|---|---|---|---|
| JP | 2000-265107 A | | 9/2000 |
| JP | 2002-256176 A | * | 9/2002 |
| JP | 2002-535255 A | | 10/2002 |
| JP | 2003-55890 A | | 2/2003 |
| JP | 2008-533237 A | | 8/2008 |
| JP | 2008-535943 A | | 9/2008 |
| JP | 2009-503229 A | | 1/2009 |
| WO | WO 2005/005516 A1 | | 1/2005 |
| WO | WO 2009/149919 A1 | | 12/2009 |

OTHER PUBLICATIONS

Extended European Search Report issued Jan. 2, 2014, in Patent Application No. 11759332.7.
International Search Report issued Apr. 19, 2011 in PCT/JP2011/056571.

* cited by examiner

*Primary Examiner* — Blessing M Fubara
(74) *Attorney, Agent, or Firm* — Oblon, Spivak, McClelland, Maier & Neustadt, L.L.P.

(57) ABSTRACT

There is provided an antifouling coating composition capable of forming an antifouling coating film which has stable coating film consumption degree on ships, underwater structures and the like and which exhibits excellent antifouling property over a long term. The antifouling coating composition includes a hydrolyzable copolymer (A) and an antifouling agent (B), wherein the hydrolyzable copolymer (A) is, e.g., a metal salt bond-containing copolymer having a component unit derived from a monomer (a21) represented by the general formula (II):

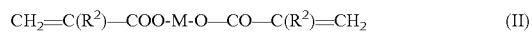

$$CH_2=C(R^2)-COO-M-O-CO-C(R^2)=CH_2 \qquad (II)$$

[In the formula (II), M is zinc or copper, and $R^2$ is a hydrogen atom or a methyl group], and a component unit derived from other unsaturated monomer (a22) copolymerizable with the monomer (a21), and wherein the antifouling agent (B) includes at least medetomidine.

16 Claims, No Drawings

ANTIFOULING COATING COMPOSITION AND USES OF THE SAME

TECHNICAL FIELD

The present invention relates to an antifouling coating composition which comprises a hydrolyzable copolymer and an antifouling agent and is employable for preventing aquatic animals from fouling a substrate. The present invention also relates to uses of the antifouling coating composition.

BACKGROUND ART

A material to coat a bottom of a ship that is now widely employed is an antifouling coating material containing a component such as a (meth)acrylic acid metal salt copolymer and a silyl ester copolymer, and various antifouling agents, for its ability to exhibit good consumption property and good antifouling property. However, in less often ship-operating, or under certain sea conditions, animals, e.g., barnacles, and slimes (microorganism coating), e.g., diatoms, adhere onto the substrate of the ship, often causing a problem.

In view of the above, conventional antifouling coating composition contained a copper compound, e.g., cuprous oxide, aimed at preventing the adhering of the barnacles and the like, or an organic antifouling agent intended as an antislime agent, e.g., N,N-dimethyl-N'-phenyl-(N-fluorodichloromethylthio)sulfamide, 2,4,6-trichlorophenylmaleimide, and 2,3,5,6-tetrachloro-4-(methylsulfonyl)pyridine.

These conventional antifouling coating compositions, however, need to contain an antifouling agent in a large amount in order to sufficiently exhibit an antifouling effect, and this has an adverse effect on coating film property.

For this reason, there has been a demand for an antifouling coating composition excellent in coating film property which has stable coating film consumption degree on ships, underwater structures and the like and which exhibits excellent antifouling property over a long term.

Patent document 1 describes the use as an antifouling component of medetomidine bonded to metal nanoparticles. Patent document 2 describes the use as an antifouling component of medetomidine bonded to a skeleton of a polymer such as polystyrene and an acrylate polymer. Patent document 3 describes a protective coating containing medetomidine and an organic antifouling agent such as 3-(3,4-dichlorophenyl)-1,1-dimethyl urea serving as an algal inhibitory substance. Patent document 4 describes the use of medetomidine as a chemical to inhibit marine biofouling, and further describes the blending of medetomidine into a coating material containing an acrylic polymer.

Still, it is difficult for these conventional antifouling coating compositions to form an antifouling coating film which has stable coating film consumption degree on ships, underwater structures and the like and which exhibits excellent antifouling property over a long term.

CITATION LIST

Patent Document

Patent document 1: JP 2008-533237 A
Patent document 2: JP 2008-535943 A
Patent document 3: JP 2009-503229 A
Patent document 4: JP 2002-535255 A

SUMMARY OF THE INVENTION

Problem to be Solved by the Invention

It is an object of the present invention to provide an antifouling coating composition capable of forming an antifouling coating film which has stable coating film consumption degree on ships, underwater structures and the like and which exhibits excellent antifouling property over a long term. It is another object of the present invention to provide uses of the antifouling coating composition.

Means for Solving the Problem

As a result of repeated studies, the present inventors have found that the use of an antifouling coating composition comprising a specific hydrolyzable copolymer, and medetomidine as an antifouling agent, can form an antifouling coating film that solves the aforesaid problem. The present invention has been accomplished based on this finding.

That is, the antifouling coating composition of the present invention is an antifouling coating composition comprising at least one hydrolyzable copolymer (A) selected from the group consisting of the following (a1) to (a3), and an antifouling agent (B) comprising at least medetomidine, (a1) a metal salt bond-containing copolymer which is an acrylic resin or a polyester resin and has a side-chain end group represented by the general formula (I):

$$—COO\text{-}M\text{-}O—COR^1 \qquad (I)$$

[In the formula (I), M is zinc or copper, and $R^1$ is an organic group];

(a2) a metal salt bond-containing copolymer having
a component unit derived from a monomer (a21) represented by the general formula (II):

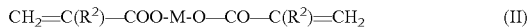

$$CH_2=C(R^2)—COO\text{-}M\text{-}O—CO—C(R^2)=CH_2 \qquad (II)$$

[In the formula (II), M is zinc or copper, and $R^2$ is a hydrogen atom or a methyl group], and
a component unit derived from other unsaturated monomer (a22) copolymerizable with the monomer (a21); and (a3) a silyl ester copolymer having
a component unit derived from a monomer (a31) represented by the general formula (III):

$$R^7—CH=C(R^3)—COO—SiR^4R^5R^6 \qquad (III)$$

[In the formula (III), $R^3$ is a hydrogen atom or a methyl group,
$R^4$, $R^5$ and $R^6$ are each independently a hydrocarbon group, and
$R^7$ is a hydrogen atom or $R^8—O—CO—$ (wherein $R^8$ is an organic group or a silyl group represented by $—SiR^9R^{10}R^{11}$, wherein $R^9$, $R^{10}$ and $R^{11}$ are each independently a hydrocarbon group)], and optionally
a component unit derived from other unsaturated monomer (a32) copolymerizable with the monomer (a31).

Preferably, an organic group $R^1$ in the metal salt bond-containing copolymer (a1) is an organic acid residue formed from a monobasic acid, and is a saturated or unsaturated aliphatic hydrocarbon group having 2 to 30 carbon atoms, a saturated or unsaturated alicyclic hydrocarbon group having 3 to 20 carbon atoms, an aromatic hydrocarbon group having 6 to 18 carbon atoms, or a substituted group thereof. More specific examples of the organic group $R^1$ include an organic acid residue formed from at least one monobasic acid selected from the group consisting of versatic acid, palmitic acid, stearic acid, oleic acid, linoleic acid, linolenic acid, abietic acid, neoabietic acid, pimaric acid, dehydroabietic acid, 12-hydroxystearic acid and naphthenic acid. With regard to the metal salt bond-containing copolymers (a1) and (a2) and the silyl ester copolymer (a3), detailed embodiments in other respects are described later.

The medetomidine is contained preferably in an amount of 0.01 to 200 parts by weight based on 100 parts by weight of the hydrolyzable copolymer (A). The antifouling coating composition of the present invention may further comprise an antifouling agent other than medetomidine such as cuprous oxide, copper pyrithione and zinc pyrithione.

An antifouling coating film of the present invention is formed from the antifouling coating composition.

In a substrate with a coating film of the present invention, a surface of the substrate is coated with a coating film obtained by curing the antifouling coating composition.

A method for producing a substrate with a coating film of the present invention comprises a step of applying or impregnating the antifouling coating composition to a surface of a substrate, and a step of curing the composition to form a coating film.

Effect of the Invention

The use of the antifouling coating composition of the present invention can form an antifouling coating film which has stable coating film consumption degree on ships, underwater structures and the like and which exhibits excellent antifouling property over a long term. Furthermore, in the present invention, the composition does not need to contain a large amount of an antifouling agent to exhibit excellent antifouling property, and thus this does not have an adverse effect on coating film property.

EMBODIMENTS FOR CARRYING OUT THE INVENTION

In the present invention, the weight of a substance serving as a standard to define a content of a component, is a weight of a component capable of forming a dried coating film which excludes a volatile component, e.g., a resin polymerization solvent and a coating material dilution solvent: in other words, a weight of a "solid component". The terms "(meth) acrylic acid" and "(meth)acrylate" collectively refer to an acrylic acid and a methacrylic acid, and acrylate and methacrylate, respectively. In the present specification, each component may be used in a single kind or in combination of two or more kinds, unless otherwise noted.

Antifouling Coating Composition

The antifouling coating composition according to the present invention comprises a hydrolyzable copolymer (A) and an antifouling agent (B).

<Hydrolyzable Copolymer (A)>

The antifouling coating composition of the present invention comprises, as a resin component, a "hydrolyzable copolymer" which is hydrolyzable in an alkali atmosphere such as in sea water (also referred to as a "hydrolyzable copolymer (A)", hereinafter). The use of the hydrolyzable copolymer (A) as a resin component can form an antifouling coating film which has stable coating film consumption degree on ships, underwater structures and like and which exhibits excellent antifouling property, e.g., crack resistance and adhesion with a substrate, and excellent surface smoothness.

The hydrolyzable copolymer (A) is at least one hydrolyzable copolymer selected from the group consisting of:
 a metal salt bond-containing copolymer (a1) (also referred to as a "copolymer (a1)" hereinafter),
 a metal salt bond-containing copolymer (a2) (also referred to as a "copolymer (a2)" hereinafter), and
 a silyl ester copolymer (a3) (also referred to as a "copolymer (a3)" hereinafter).

The hydrolyzable copolymer (A) may be a copolymer satisfying requirements of both the copolymer (a1) and the copolymer (a2), i.e., a copolymer containing a structure of a side-chain end metal salt bond as seen in the copolymer (a1) and a structure of a crosslinked metal salt bond as seen in the copolymer (a2).

The hydrolyzable copolymer (A) may be used in a single kind or in combination of two or more kinds.

Metal Salt Bond-Containing Copolymer (a1)

The metal salt bond-containing copolymer (a1) is an acrylic resin or a polyester resin, and is a metal salt bond-containing copolymer having a side-chain end group represented by the general formula (I). In the present invention, the above structure is also referred to as a "side-chain end metal salt bond".

$$—COO\text{-}M\text{-}O—COR^1 \quad (I)$$

In the formula (I), M is zinc or copper, and $R^1$ is an organic group. In the copolymer (a1), usually, plural side-chain end groups each represented by the formula (I) are present, and each of $R^1$ may be the same as or different from one another, and each of M may be the same as or different from one another.

Preferably, the organic group $R^1$ in the copolymer (a1) (an organic group $R^1$ in the formula (IV) described later) is an organic acid residue formed from a monobasic acid, and is a saturated or unsaturated aliphatic hydrocarbon group having 2 to 30 carbon atoms, a saturated or unsaturated alicyclic hydrocarbon group having 3 to 20 carbon atoms, an aromatic hydrocarbon group having 6 to 18 carbon atoms, or substituted groups thereof; more preferably a saturated or unsaturated aliphatic hydrocarbon group having 10 to 20 carbon atoms, a saturated or unsaturated alicyclic hydrocarbon group having 3 to 20 carbon atoms, or substituted groups thereof. An example of the substituted group is a hydroxyl group substituted group. Of these, particularly preferable are organic acid residues formed from at least one monobasic acid selected from the group consisting of versatic acid, palmitic acid, stearic acid, oleic acid, linoleic acid, linolenic acid, (including structural isomers of these unsaturated aliphatic acids, e.g., isostearic acid; the same applies hereinafter.), abietic acid, neoabietic acid, pimaric acid, dehydroabietic acid, 12-hydroxystearic acid and naphthenic acid. The copolymer (a1) having such $R^1$ is easy to prepare, and the use of the copolymer (a1) having such $R^1$ can provide an antifouling coating film with much superior hydrolysis property and recoatability.

<Acrylic Resin Type>

Among the copolymer (a1), an acrylic resin type polymer is preferable. In the copolymer (a1), the acrylic resin type polymer can be prepared, for example, through polymerization reaction using a metal salt bond-containing monomer represented by the general formula (IV), i.e., a monobasic acid metal (meth)acrylate (also referred to as a "monomer (a11)" hereinafter).

$$CH_2=C(R^2)—COO\text{-}M\text{-}O—COR^1 \quad (IV)$$

In the formula (IV), M is zinc or copper, $R^1$ is an organic group, and $R^2$ is a hydrogen atom or a methyl group (the same definitions as in the formulae (I) and (II)). The definition and preferred types of $R^1$ in the formula (IV) are the same as those described with regard to the organic group $R^1$ in the formula (I), with the proviso that $R^1$ in the formula (IV) is not a vinyl group [—CH=CH$_2$] and an isopropenyl group [—C(CH$_3$)=CH$_2$], in order to be distinguished from a monomer (a21) represented by the formula (II) capable of forming a crosslinked metal salt bond, which is described later.

The copolymer (a1) may be a polymer obtained through copolymerization reaction between two or more kinds of monomers (a11), or may be a polymer obtained through copolymerization reaction between one kind, or two or more kinds of monomers (a11), and one kind, or two or more kinds of "other unsaturated monomers" copolymerizable with the monomer (a11) (also referred to as a "monomer (a12)", hereinafter), i.e., a copolymer containing a component unit derived from the monomer (a11) and a component unit derived from the monomer (a12).

The monomer (a12) is arbitrarily selectable from various compounds used as polymerizable unsaturated monomers for acrylic resins, and preferred examples thereof include a monomer not containing a metal salt bond, e.g., alkyl(meth)acrylates, alkoxyalkyl(meth)acrylates, and hydroxyalkyl (meth)acrylates. Of these, particularly preferred are methyl (meth)acrylate, ethyl(meth)acrylate, butyl(meth)acrylate, 2-methoxyethyl(meth)acrylate, 3-methoxybutyl(meth)acrylate and 2-hydroxyethyl(meth)acrylate, and so on.

The acrylic resin type copolymer (a1) can be also prepared, for example, by a method comprising preparing an acrylic resin by using a (meth)acrylic acid, an alkyl(meth)acrylate, an alkoxyalkyl(meth)acrylate, a hydroxyalkyl(meth)acrylate, etc., and then performing a reaction which introduces a structure having an organic group ($R^1$) bonded to a carboxyl group through zinc or copper (M), wherein the carboxyl group is present at a side chain of the acrylic resin where a metal salt bond has not yet been formed, thereby forming a side-chain end group represented by the formula (I).

<Polyester Resin Type>

Among the copolymer (a1), a polyester resin type polymer is a polyester resin which is synthesized from a polybasic acid and a polyhydric alcohol as a main raw material, and has an acid value of 50 to 200 mgKOH/g, preferably 80 to 170 mgKOH/g, and which has, at its end, a side-chain end group represented by the formula (I).

Examples of the acid component to generate the polyester resin include monocarboxylic acids such as benzoic acid and p-t-butyl benzoic acid; dicarboxylic acids and anhydrides thereof such as terephthalic acid, isophthalic acid, phthalic anhydride, 1,4-naphthol acid, diphenic acid, 4,4'-oxybenzoic acid, 2,5-naphthalenedicarboxylic acid, tetrahydrophthalic acid, tetrahydrophthalic anhydride, norbornenedicarboxylic acid, oxalic acid, malonic acid, dimethylmalonic acid, succinic acid, glutaric acid, adipic acid, azelaic acid, sebacic acid, 1,3-cyclohexyldicarboxylic acid; and alkyl esters having about 1 to 4 carbon atoms of these dicarboxylic acids. These may be used in a single kind or in combination of two or more kinds. Along with these examples, trifunctional or more carboxylic acids such as trimellitic acid, trimellitic anhydride, pyromellitic acid and pyromellitic anhydride, may be used, and a slight amount of unsaturated dicarboxylic acids and esters thereof such as maleic anhydride, maleic acid, itaconic anhydride, itaconic acid and fumaric acid may be used in combination.

Examples of the polyhydric alcohol component to generate the polyester resin include ethylene glycol, diethylene glycol, triethylene glycol, polyethylene glycol, 1,2-propylene glycol, 1,3-propylene glycol, dipropylene glycol, polypropylene glycol, neopentyl glycol, 1,5-pentane diol, 1,6-hexane diol, 3-methyl-1,5-pentane diol, 2-methyl-1,3-propane diol, 2,2-diethyl-1,3-propane diol, 2-butyl-2-ethyl-1,3-propane diol, bisphenol A, and a hydrogenated bisphenol A. These may be used in a single kind or in combination of two or more kinds. Along with these, trifunctional or more alcohols such as trimethylolethane, glycerin and pentaerythritol may be used in combination.

The polyester resin type copolymer (a1) can be prepared, for example, by a method comprising carrying out esterification reaction or ester exchange reaction by a known process such as a dissolution process using these various acid components and alcohol components thereby preparing a polyester resin, and then performing a reaction which introduces a structure having an organic group ($R^1$) bonded to a carboxyl group through zinc or copper (M), wherein the carboxyl group is present at the end where a metal salt bond has not yet been formed, thereby forming a side-chain end group represented by the formula (I).

In the case of introducing the prescribed side-chain end group into the acrylic resin or the polyester resin by the preparation method as described above, too, preferable types of $R^1$ in the formula (I) are the same as those previously described. In the preparation method as describe above, the monobasic acids as described above can be used for a reaction to introduce the organic group $R^1$.

In the copolymer (a1), zinc and/or copper attributed to the structure of the formula (I) is contained preferably in an amount of 0.5 to 20% by weight, more preferably 1 to 19% by weight of the copolymer. The use of the copolymer (a1) fulfilling such requirements can form an antifouling coating film much superior both in antifouling property and in consumption property. The "amount of zinc and/or copper" as used herein refers to a total amount of zinc and copper if both zinc and copper are contained.

The amount of zinc and/or copper can be within the above range, for example, by controlling the blending ratio between the monomer (a11) containing these metals and the monomer (a12) which are used for the preparation of the copolymer (a1), or the addition amount of the compound (e.g., the monobasic acid as described above) containing zinc and/or copper to be reacted with the acrylic resin or the polyester resin previously prepared.

Metal Salt Bond-Containing Copolymer (a2)

The metal salt bond-containing copolymer (a2) is a copolymer having a component unit derived from a monomer (a21) represented by the general formula (II) and a component unit derived from "other unsaturatedmonomer (a22)" copolymerizable with the monomer (a21).

$$CH_2=C(R^2)-COO-M-O-CO-C(R^2)=CH_2 \quad \text{(II)}$$

In the formula (II), M is zinc or copper, and $R^2$ is a hydrogen atom or a methyl group. In the copolymer (a2), usually, plural component units each derived from the monomer (a21) represented by the formula (II) are present, and each of $R^2$ may be the same as or different from one another, and each of M may be the same as or different from one another.

Examples of the monomer (a21) include zinc diacrylate, zinc dimethacrylate, copper diacrylate, and copper dimethacrylate. The monomer (a21) may be used in a single kind or in combination of two or more kinds.

The monomer (a21) can be prepared by a known method, such as a method in which an inorganic metal compound (e.g., an oxide, a hydroxide, a chloride, etc. of zinc or copper), and a (meth)acrylic acid or its ester compound are heated and stirred, at not higher than a temperature at which a metal sat is decomposed, in the presence of an alcohol based organic solvent and water.

The component unit derived from the monomer (a21) has a structure represented by the general formula (V), and this structure is also referred to as a "crosslinked metal salt bond" in the present invention.

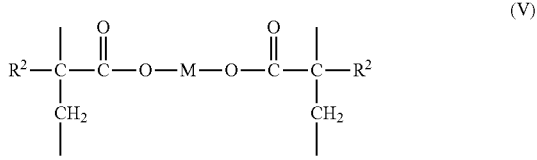

The "other unsaturated monomer (a22)" copolymerizable with the monomer (a21) is arbitrarily selectable from various compounds employed as polymerizable unsaturated monomers for acrylic resins, as is the case with the monomer (a12) in connection with the copolymer (a1). Preferred examples of the unsaturated monomer (a22) include alkyl(meth)acrylates, alkoxyalkyl(meth)acrylates, and hydroxyalkyl(meth)acrylates. Of these, particularly preferred are methyl(meth)acrylate, ethyl(meth)acrylate, butyl(meth)acrylate, 2-methoxyethyl(meth)acrylate, 3-methoxybutyl(meth)acrylate and 2-hydroxyethyl(meth)acrylate.

The monomer (a11), described above in connection with the copolymer (a1), i.e., the monobasic acid metal (meth)acrylate represented by the formula (IV), too, is a monomer copolymerizable with the monomer (a21), and thus corresponds to the monomer (a22), employable for the preparation of the metal salt bond-containing copolymer (a2). With regard to the monobasic acid metal (meth)acrylate represented by the formula (IV) as the unsaturated monomer (a22), too, the definition and preferred embodiments of $R^1$ are the same as those described with regard to the organic group $R^1$ in the formula (I).

The unsaturated monomer (a22) may be used in a single kind or in combination of two or more kinds.

In another preferable embodiment, the unsaturated monomer (a22) comprises the monobasic acid metal (meth)acrylate represented by the formula (IV) and at least one unsaturated monomer selected from the group consisting of an alkyl (meth)acrylate, an alkoxyalkyl(meth)acrylate, and a hydroxyalkyl(meth)acrylate.

Further examples of the unsaturated monomer (a22) include styrene and styrene derivatives; vinyl esters such as vinyl acetate and vinyl propionate; (meth)acrylamide and derivatives thereof; and (meth)acrylonitrile.

In the copolymer (a2), too, zinc and/or copper attributed to the structure of the formula (II) is contained preferably in an amount of 0.5 to 20% by weight, more preferably 1 to 19% by weight of the copolymer, from the same viewpoint as described with regard to the copolymer (a1). The "amount of zinc and/or copper" as used herein refers to a total amount of zinc and copper if both zinc and copper are contained.

The amount of zinc and/or copper can be within the above range, for example, by controlling the blending ratio of monomers employed for the preparation of the copolymer (a2). When the copolymer (a2) has a structure of the crosslinked metal salt bond and a structure of the side-chain end metal salt bond, it is preferable that the total amount of zinc and/or copper attributed to each structure is controlled so as to be within the above range.

The number-average molecular weight (Mn: in terms of polystyrene) and the weight-average molecular weight (Mw: in terms of polystyrene) of the copolymer (a1) and the copolymer (a2) can be arbitrarily adjusted in view of a viscosity and a storage stability of the antifouling coating composition and an elution rate of the antifouling coating film, etc., and Mn is usually about 1,000 to 100,000, preferably 1,000 to 50,000, and Mw is usually about 1,000 to 200,000, preferably 1,000 to 100,000.

Silyl Ester Copolymer (a3)

The silyl ester copolymer (a3) is a copolymer having a component unit (also referred to as a "silyl ester component unit" hereinafter) derived from a monomer (a31) represented by the general formula (III) (also referred to as a "silyl ester monomer" hereinafter), and the copolymer optionally has a component unit derived from other unsaturated monomer (a32) copolymerizable with the monomer (a31).

In the formula (III), $R^3$ is a hydrogen atom or a methyl group, $R^4$, $R^5$ and $R^6$ are each independently a hydrocarbon group, and $R^7$ is a hydrogen atom or $R^8$—O—COO— (wherein $R^8$ is an organic group or a silyl group represented by —$SiR^9R^{10}R^{11}$, wherein $R^9$, $R^{10}$ and $R^{11}$ are each independently a hydrocarbon group).

The silyl ester monomer (a31) wherein $R^7$ is a hydrogen atom (H) is represented by the general formula (IIIa):

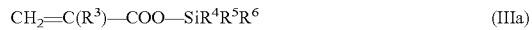

In the formula (IIIa), $R^3$, $R^4$, $R^5$ and $R^6$ are the same as $R^3$, $R^4$, $R^5$ and $R^6$, respectively, in the formula (III).

The hydrocarbon group in the $R^4$, $R^5$ and $R^6$ is preferably an alkyl group having 1 to 10 carbon atoms, particularly 1 to 5 carbon atoms, and more preferably, an alkyl group such as methyl, ethyl, propyl and isopropyl.

Examples of a silyl ester monomer (a33), represented by the formula (IIIa), include trialkylsilyl(meth)acrylates such as trimethylsilyl(meth)acrylate, triethylsilyl(meth)acrylate and triisopropylsilyl(meth)acrylate. Of these, triisopropylsilyl(meth)acrylate is preferable, which provides excellent elution of a resin from the coating film, long-lasting elution property of a resin and coating film property (e.g., crack resistance).

The silyl ester monomer (a31) wherein $R^7$ is "$R^8$—O—CO—" is represented by the formula (IIIb):

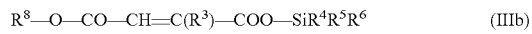

In the formula (IIIb), $R^3$, $R^4$, $R^5$, $R^6$ and $R^8$ are the same as $R^3$, $R^4$, $R^5$, $R^6$ and $R^8$, respectively in the formula (III) or the formula (IIIa).

The organic group in the $R^8$ is preferably an alkyl group having 1 to 10 carbon atoms, particularly 1 to 5 carbon atoms, more preferably an alkyl group such as methyl, ethyl, propyl and isopropyl. The hydrocarbon group in the $R^9$, $R^{10}$ and $R^{11}$ is preferably an alkyl group having 1 to 10 carbon atoms, particularly 1 to 5 carbon atoms, more preferably an alkyl group such as methyl, ethyl, propyl and isopropyl.

An example of a silyl ester monomer (a34), represented by the formula (IIIb), is a maleate (a compound represented by the formula (IIIb) wherein $R^3$ is H).

Examples of the other unsaturated monomer (a32) copolymerizable with the monomer (a31) (or with the monomer (a33) and/or the monomer (a34)) include the "other unsaturated monomer (a12)" and the "other unsaturated monomer (a22)" exemplified as raw materials compound of the copolymer (a1) and the copolymer (a2), respectively.

Preferred examples of the other unsaturated monomer (a32) include alkyl(meth)acrylates, alkoxyalkyl(meth)acrylates, and hydroxyalkyl(meth)acrylates. Of these, particularly preferable are methyl(meth)acrylate, ethyl(meth)acrylate, butyl(meth)acrylate, 2-methoxyethyl(meth)acrylate, 3-methoxybutyl(meth)acrylate and 2-hydroxyethyl(meth)acrylate.

The silyl ester monomer (a31) may be used in a single kind or in combination of two or more kinds. The other unsaturated monomer (a32) may be used in a single kind or in combination of two or more kinds.

In the silyl ester copolymer (a3), the component unit derived from the silyl ester monomer (a31) is contained usually in an amount of 10 to 100% by mol, preferably 10 to 90% by mol, and the component unit derived from the "other unsaturated monomer (a32)" is contained in a residual amount, that is, usually in an amount of 0 to 90% by mol, preferably 10 to 90% by mol, based on 100% by mol of all constituents in the copolymer. The amounts of the component units being within the above range are preferable, which provides excellent viscosity of a resin in the coating film (e.g., crack resistance), storage stability of the coating material, elution of a resin from the coating film, etc.

The number-average molecular weight Mn (in terms of polystyrene) of the silyl ester copolymer (a3) is usually 1,000 to 200,000, preferably 1,000 to 100,000. Mn being within the above range is preferable, which provides excellent viscosity of a resin in the coating film (e.g., crack resistance), storage stability of the coating material, elution of a resin from the coating film, etc.

In the antifouling coating composition of the present invention, the hydrolyzable copolymer (A) is contained in terms of a solid component preferably in an amount of 0.1 to 99.999% by weight, more preferably 1 to 99.999% by weight, most preferably 3 to 99.999% by weight.

<Antifouling Agent (B)>

The antifouling coating composition of the present invention comprises medetomidine as an antifouling agent (B).

Medetomidine (system name: (±)4-[1-(2,3-dimethylphenyl)ethyl]-1H-imidazole) is a compound represented by the following structural formula.

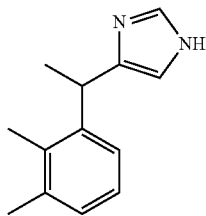

The use of medetomidine with the metal salt bond-containing hydrolyzable copolymer (A) can provide an antifouling coating composition excellent in coating film property which has stable coating film consumption degree on ships, underwater structures and the like and which exhibits excellent antifouling property over a long term.

The amount of medetomidine contained in the antifouling coating composition of the present invention is preferably 0.01 to 200 parts by weight, more preferably 0.02 to 100 parts by weight, most preferably 0.05 to 50 parts by weight, based on 100 parts by weight of the hydrolyzable copolymer (A).

By satisfying these requirements, the antifouling coating composition of the present invention becomes more desirable in terms of an antifouling effect. Specifically, the antifouling coating composition comprising the hydrolyzable copolymer (A) and medetomidine, in spite of using a small amount of the antifouling agent (medetomidine) (for example, about 0.01 to 10 parts by weight, preferably about 0.01 to 2.0 parts by weight), can exhibit an antifouling effect over a long term. In the present invention, the composition does not need to contain a large amount of an antifouling agent as described above, and thus this does not have an adverse effect on coating film property such as crack resistance. Meanwhile, the antifouling effect is exhibited over a long term even if medetomidine is contained in an amount of some degree (for example, about more than 10 parts by weight to not more than 200 parts by weight).

The antifouling coating composition of the present invention, by containing medetomidine as the antifouling agent (B), exhibits much superior antifouling property. The antifouling coating composition of the present invention may optionally contain an antifouling agent, in addition to medetomidine, in order to have still more improved antifouling property.

Examples of the antifouling agent other than medetomidine include cuprous oxide, copper rhodanide, bis(2-pyridinethiol-1-oxide) copper salt (also referred to as "copper pyrithione" hereinafter), bis(2-pyridinethiol-1-oxide) zinc salt (also referred to as "zinc pyrithione" hereinafter), 4,5-dichloro-2-n-octyl-4-isothiazoline-3-one, triphenylboron.amine complex, dichloro-N-((dimethylamino)sulfonyl)fluoro-N-(p-tolyl)methane sulfeneamide, and 2-(p-chlorophenyl)-3-cyano-4-bromo-5-trifluoromethylpyrrol.

Further examples thereof include inorganic antifouling agents such as inorganic copper compounds, e.g., copper powders; and organic antifouling agents such as N,N-dimethyldichlorophenyl urea, 2,4,6-trichlorophenyl maleimide, 2-methylthio-4-tert-butylamino-6-cyclopropyl-S-triazine, 2,4,5,6-tetrachloroisophthalonitrile, bisdimethyldithiocarbamoyl zinc ethylene bisdithiocarbamate, chloromethyl-n-octyldisulfide, N,N'-dimethyl-N'-phenyl-(N-fluorodichloromethylthio)sulfamide, tetraalkylthiuramdisulfide, zinc dimethyldithio carbamate, zinc ethylene bisdithio carbamate, 2,3-dichloro-N-(2',6'-diethylphenyl)maleimide, and 2,3-dichloro-N-(2'-ethyl-6'-methylphenyl)maleimide.

These antifouling agents may be used in a single kind or in combination of two or more kinds.

The amount of the antifouling agent other than medetomidine contained in the antifouling coating composition of the present invention is not particularly limited as long as being within a range which does not have an adverse effect on coating film property such as crack resistance, and is preferably 0 to 15000 parts by weight, more preferably 1 to 3000 parts by weight, still more preferably 5 to 1500 parts by weight, most preferably 10 to 500 parts by weight, based on 100 parts by weight of the hydrolyzable copolymer (A). The amount of the antifouling agent other than medetomidine is preferably 0 to 600000 parts by weight, more preferably 100 to 200000 parts by weight, most preferably 200 to 100000 parts by weight, based on 100 parts by weight of medetomidine.

<Other Components>

The antifouling coating composition of the present invention can comprise, in addition to the aforesaid components, various components used in a general coating composition, such as color pigments, extender pigments, dehydrating agents, plasticizers, thixotropic agents, resins other than the hydrolyzable copolymer (A), organic acids, and solvents. These may be used in a single kind or in combination of two or more kinds.

Color Pigment

Examples of the color pigment include inorganic pigments such as red iron oxide, titanium white (titanium oxide) and yellow iron oxide; and organic pigments such as carbon black, naphthol red and phthalocyanine blue. The color pigment may be used in a single kind or in combination of two or more kinds. The color pigment may further contain various colorants such as dye. The blending amount of the color pigment can be arbitrarily adjusted, and is preferably 0.05 to 250 parts by weight, more preferably 1 to 125 parts by weight, based on 100 parts by weight of the hydrolyzable copolymer (A).

Extender Pigment

The extender pigment is a pigment of a low refractive index that is transparent and does not hide the coated surface when mixed with an oil or a varnish. Examples of the extender pigment include talc, silica, mica, clay, zinc oxide, calcium carbonate that is used also as an anti-settling agent, kaolin, alumina white, white carbon that is used also as a flatting agent, aluminum hydroxide, magnesium carbonate, barium carbonate, barium sulfate and zinc sulfide. Of these, preferable are zinc oxide, talc, silica, mica, clay, calcium carbonate, kaolin and barium carbonate. The extender pigment may be used in a single kind or in combination of two or more kinds. The blending amount of the extender pigment can be arbitrarily adjusted, and is preferably 0.5 to 750 parts by weight, more preferably 5 to 400 parts by weight, most preferably 10 to 250 parts by weight, based on 100 parts by weight of the hydrolyzable copolymer (A).

Dehydrating Agent

The dehydrating agent is a component that contributes to the improvement of the storage stability of the coating material. Examples of the dehydrating agent include inorganic ones including anhydrite, hemihydrate gypsum (exsiccated gypsum), and a synthetic zeolite based adsorbent (e.g., a product named "molecular sieve"). Further examples include orthoesters (e.g., methyl orthoformate, methyl orthoacetate, and orthoboric acid ester), silicates, and isocyanates. Of these, anhydrite and hemihydrate gypsum (exsiccated gypsum), each of which is an inorganic dehydrating agent, are preferred. The dehydrating agent may be used in a single kind or in combination of two or more kinds. The blending amount of the dehydrating agent can be arbitrarily adjusted, and is preferably 0 to 100 parts by weight, more preferably 0.5 to 25 parts by weight, based on 100 parts by weight of the hydrolyzable copolymer (A).

Plasticizer

The plasticizer is a component that contributes to the improvement of crack resistance and water resistance and the inhibition of discoloration of the antifouling coating film. Examples of the plasticizer include n-paraffin, chlorinated paraffin, terpene phenol, tricresyl phosphate (TCP), and polyvinyl ethyl ether. Of these, chlorinated paraffin and terpene phenol are preferable; and chlorinated paraffin is particularly preferable. The plasticizer may be used in a single kind or in combination of two or more kinds. As the n-paraffin, an example of a commercial product employable is "n-paraffin", manufactured by Nippon Petrochemicals Co., Ltd. As the chlorinated paraffin, examples of commercial products employable are "Toyoparax A-40/A-50/A-70/A-145/A-150", manufactured by Tosoh Corporation. The blending amount of the plasticizer can be arbitrarily adjusted, and is preferably 0.5 to 10% by weight, more preferably 1 to 5% by weight, based on 100% by weight of all solid components including the plasticizer in the antifouling coating composition.

Anti-Sagging/Anti-Settling Agent

Examples of the anti-sagging/anti-settling (thixotropic agent) include organic clay compounds (e.g., an amine salt, a stearate salt, a lecithin salt and an alkyl sulfonate of Al, Ca and Zn), organic waxes (e.g., polyethylene wax, oxidized polyethylene wax, polyamide wax, amide wax, and hydrogenated castor oil wax), and synthetic finely divided silica. Of these, preferable are the organic clay compounds, polyamide wax, amide wax, oxidized polyethylene wax, and synthetic finely divided silica. The anti-sagging/anti-settling agent may be used in a single kind or in combination of two or more kinds. The blending amount of the anti-sagging/anti-settling agent can be arbitrarily adjusted, and is, for example, 0.25 to 50 parts by weight based on 100 parts by weight of the hydrolyzable copolymer (A).

Other Resins and Organic Acids

The antifouling coating composition of the present invention may comprise one kind, or two or more kinds of other resins, in addition to the metal salt bond-containing copolymer (A) as described above.

Employable examples include water-insoluble resins or poorly water-soluble resins, such as an acrylic resin not containing a metal salt bond, an acrylic silicone resin, a polyester resin, an unsaturated polyester resin, a fluororesin, a polybutene resin, a silicone rubber, a polyurethane resin, an epoxy resin, a polyamide resin, a vinyl resin (e.g., a vinyl chloride copolymer and an ethylene/vinyl acetate copolymer), a chlorinated rubber, a chlorinated olefin resin, a styrene/butadiene copolymer resin, a ketone resin, an alkyd resin, a coumarone resin, a terpene phenol resin and a petroleum resin.

Further examples employable with the hydrolyzable copolymer (A) include water-soluble resins such as pine tar, rosin (gum rosin, wood rosin and tall oil rosin), and monobasic organic acids such as naphthenic acid, versatic acid, triphenylisobutenyl cyclohexene carboxylic acid ("A-3000" manufactured by Yasuhara Chemical Co., Ltd.).

Solvent

Various components constituting the antifouling coating composition of the present invention are usually dissolved or dispersed in a solvent, as is the case with a general antifouling coating composition. A solvent employable in the present invention can be a solvent generally used for an antifouling coating material, the examples of which include an aliphatic solvent, an aromatic solvent (e.g., xylene and toluene), a ketone solvent (e.g., MIBK and cyclohexanone), an ester solvent, an ether solvent (e.g., propylene glycol monomethyl ether and propylene glycol monomethyl ether acetate), and an alcohol solvent (e.g., isopropyl alcohol). The blending amount of the solvent can be arbitrarily adjusted, and is, for example, such an amount that all solid components account for 20 to 90% by weight in the antifouling coating composition. The solvent may be further added in coating operation in view of workability.

[Production Method and Uses of Antifouling Coating Composition]

The antifouling coating composition of the present invention can be prepared with apparatus, means, etc. similar to those employed for generally known antifouling coating materials. For example, the metal salt bond-containing copolymer (a1) or (a2), or the silyl ester copolymer (a3) is prepared in advance, and then this copolymer (reaction liquid) and the antifouling agent (B), optionally with other components such as additives, are added into a solvent, at a time or in series, and stirred and mixed.

The antifouling coating composition of the present invention can be used in embodiments similar to those for generally known antifouling coating materials, and the antifouling coating film of the present invention is formed from the antifouling coating composition. For example, a surface of a substrate is coated or impregnated with the antifouling coating composition of the present invention, and then dried for a prescribed period of time, thereby forming a cured antifouling coating film on the surface of the substrate.

For example, in a substrate with a coating film (e.g., an antifouling substrate) of the present invention, a surface of the substrate is coated with a coating film obtained by curing the antifouling coating composition;

a method for producing a substrate with a coating film of the present invention comprises a step of applying or impregnating the antifouling coating composition to a surface of a substrate, and a step of curing the composition to form a coating film; and a method for preventing a substrate from fouling of the present invention comprises a step of applying or impregnating the antifouling coating composition to a surface of a substrate, and a step of curing the composition to form an antifouling coating film.

Examples of the substrate include a substrate which is (e.g., always or intermittently) in contact with seawater or fresh water, and more specific examples include an underwater structure, an outside board of a ship, a fishing net and a fishing gear.

The surface of the substrate, by being coated with such an antifouling coating film, can be prevented for a long term from fouling caused by aquatic animals. The (dried) thickness of the antifouling coating film can be arbitrarily adjusted in view of consumption rate of the coating film, etc. Exemplary thickness thereof is 40 to 400 μm per one coating, preferably about 40 to 200 μm per one coating.

EXAMPLES

Hereinafter, the present invention is further described with reference to Examples, but it should be construed that the present invention is in no way limited to these Examples. In the following Examples and Comparative Examples, the term "part(s)" means part(s) by weight, and "%" with respect to the indication of a solid component means % by weight, unless deviating from the point.

In the present invention, including tables as described later, a mere reference, e.g., to "copolymer (A)" basically means a "resin" which is a coating film-forming component. The reference e.g., to "copolymer (A)" with the indication of a solid component also means a "resin solution or dispersion" containing a volatile component such as a solvent as well as the resin serving as the coating film-forming component.
<Measurement Conditions of Gardner Viscosity>

Gardner viscosity was measured under the conditions of a resin concentration of 35% by weight and 25° C. in accordance with JIS K 7233-4.3, as described in JP 2003-55890 A.
<Viscosity>

The viscosity at 25° C. was measured with a B-type viscometer.
<Solid Component>

A solid component means a heating residue given when a reaction mixture, a coating material, an uncured coating film or the like containing a polymer, a solvent, etc. is heated and dried for 3 hours in a drier of heated air at 105° C. to evaporate the solvent, etc. The solid component usually includes a resin, a pigment, etc. and becomes a coating film-forming component. For the calculation, monomers (examples: Table 2) contained in the coating material or the like and capable of forming a resin (solid component) through reaction are also included in the solid component.
<Measurements of Number-Average Molecular Weight (Mn) and Weight-Average Molecular Weight (Mw)>

Weight-average molecular weight (Mw) of a resin was measured by gel permeation chromatography (GPC) method with "HLC-8120GPC", manufactured by Tosoh Corporation, using two separation columns (α-M) of "TSK-gel α type", manufactured by Tosoh Corporation, and using, as an eluting solution, dimethylformamide (DMF) to which 20 mM of LiBr had been added. The weight-average molecular weight of the resin was determined in terms of polystyrene. Number-average molecular weight (Mn) of the resin was measured by GPC as described above and determined in terms of polystyrene.

Production Example 1

Production of Side-Chain End Metal Salt Bond-Containing Copolymer (a1-1)

Into a four-necked flask equipped with a condenser, a thermometer, a dropping funnel and a stirrer, 30 parts of propylene glycol monomethyl ether (PGM) and 40 parts of xylene were introduced, and with stirring, they were heated to 100° C. Subsequently, from the dropping funnel, a mixture consisting of monomers and a polymerization initiator shown in Table 1 was dropped at a constant rate over 3 hours. After the dropping was completed, 1 part of t-butyl peroctoate and 10 parts of xylene were dropped over 2 hours, and after stirring for 2 hours, 20 parts of xylene was added, to thereby obtain a reaction mixture containing a side-chain end metal salt bond-containing copolymer (a1-1).

The Gardner viscosity and the solid component (O), which are property values of the copolymer (a1-1) or the reaction mixture containing the copolymer (a1-1) obtained, were evaluated. The results are set forth in Table 1.

TABLE 1

Production Example of side-chain end metal salt bond-containing copolymer (a1)

| Side-chain end metal salt bond-containing copolymer (a1) | | Production Example 1 a1-1 |
|---|---|---|
| Monobasic acid metal (meth)acrylate: monomer (a11) | versatic acid zinc methacrylate | 35 |
| Other unsaturated monomer copolymerizable with monomer (a11): monomer (a12) | 2-methoxyethyl acrylate | 10 |
| | 3-methoxybutyl acrylate | 30 |
| | ethyl acrylate | 25 |
| Polymerization initiator | t-butyl peroxide | 6 |
| Property values | Gardner viscosity | +Z |
| | Solid component (%) | 50.5 |

*The values of the monomer (a11), the monomer (a12) and the polymerization initiator denote parts by weight.

Preparation Example 1

Preparation of Metal-Containing Monomer (a21-1)

Into a four-necked flask equipped with a condenser, a thermometer, a dropping funnel and a stirrer, 85.4 parts of propylene glycol monomethyl ether (PGM) and 40.7 parts of zinc oxide were introduced, and with stirring, they were heated to 75° C. Subsequently, from the dropping funnel, a mixture consisting of 43.1 parts of methacrylic acid (MAA), 36.1 parts of acrylic acid (AA) and 5 parts of water was dropped at a constant rate over 3 hours. After the dropping was completed, the reaction solution turned transparent from an opaque white state. After stirring for 2 hours, 36 parts of propylene glycol monomethyl ether was added, to thereby obtain a reaction liquid containing a metal-containing monomer (a21-1). The charged amounts of the raw materials are set forth in terms of molar ratio, and the composition of the resultant reaction liquid is set forth in terms of weight percentage in Table 2.

TABLE 2

Preparation of metal-containing monomer (a21-1)

| | Charged amount (molar ratio) | | | | Volatile component (%) of reaction liquid containing metal-containing monomer | | Solid component (%)* of reaction liquid containing metal-containing monomer |
|---|---|---|---|---|---|---|---|
| | MMA | AA | ZnO | water | PGM | water | solid component |
| Preparation Example 1 a21-1 | 0.5 | 0.5 | 0.5 | 0.27 | 53.2 | 2 | 44.8 |

*Solid component (%) contains a monomer capable of forming a resin through reaction.

Production Example 2

Production of Crosslinked Metal Salt Bond-Containing Copolymer (a2-1)

Into a four-necked flask equipped with a condenser, a thermometer, a dropping funnel and a stirrer, 15 parts of propylene glycol monomethyl ether (PGM) and 57 parts of xylene were introduced, and with stirring, they were heated to 100° C. Subsequently, from the dropping funnel, a transparent mixture consisting of 52 parts of the reaction liquid of the metal-containing monomer (a21-1) obtained in Preparation Example 1, 1 part of methyl methacrylate (MMA), 66.2 parts of ethyl acrylate (EA), 5.4 parts of 2-methoxyethyl acrylate (2-MEA), 2.5 parts of azobisisobutyronitrile (AIBN, manufactured by Japan Hydrazine Company Inc.), 7 parts of azobismethylbutyronitrile (AMBN, manufactured by Japan Hydrazine Company Inc.), 1 part of a chain transfer agent ("Nofiner MSD", manufactured by Nippon Oil & Fats Co., Ltd.), and 10 parts of xylene was dropped at a constant rate over 6 hours. After the dropping was completed, 0.5 part of t-butyl peroctoate (TBPO) and 7 parts of xylene were dropped over 30 minutes. After stirring for 1 hour and 30 minutes, 4.4 parts of xylene was added, to thereby obtain an insoluble-free, light yellow, transparent reaction mixture containing a crosslinked metal salt bond-containing copolymer (a2-1). Blending composition and property values of the copolymer (a2-1) or the reaction mixture containing the copolymer (a2-1) obtained are set forth in Table 3.

TABLE 3

Production Example of crosslinked metal salt bond-containing copolymer (a2)

| Crosslinked metal salt bond-containing copolymer (a2) | | Production Example 2 a2-1 |
|---|---|---|
| Reaction liquid of metal-containing monomer: monomer (a21) | a21-1 | 52 |
| Other unsaturated monomer copolymerizable with monomer (a21): monomer (a22) | MMA | 1 |
| | EA | 66.2 |
| | 2-MEA | 5.4 |
| Initiator | AIBN | 2.5 |
| | AMBN | 7 |
| | TBPO | 0.5 |
| Chain transfer agent | Nofmer MSD | 1 |
| Property values | Gardner viscosity | –Y |
| | Solid component (%) | 45.6 |
| | Number-average molecular weight (Mn) | 1950 |
| | Weight-average molecular weight (Mw) | 5200 |

Production Example 3

Production of Crosslinked Metal Salt Bond-Containing Copolymer (a2-2)

A crosslinked metal salt bond-containing copolymer (a2-2) was prepared in the same manner as in Production Example 1, except that the blending components of the mixture containing the monomers and the polymerization initiator were changed as shown in Table 4. Blending composition and property values of the copolymer (a2-2) or the reaction mixture containing the copolymer (a2-2) obtained are set forth in Table 4.

TABLE 4

Production Example of crosslinked metal salt bond-containing copolymer (a2)

| Crosslinked metal salt bond-containing copolymer (a2) | | Production Example 3 a2-2 |
|---|---|---|
| Metal-containing monomer (a21) | Zinc diacrylate | 8 |
| | Zinc dimethacrylate | 8 |
| Monobasic acid metal (meth)acrylate: monomer (a22) | isostearic acid zinc acrylate | 12 |
| | isostearic acid zinc methacrylate | 12 |
| Other unsaturated monomer copolymerizable with monomer (a21): monomer (a22) | 2-methoxyethyl acrylate | 13 |
| | methyl methacrylate | 13 |
| | ethyl acrylate | 34 |
| Polymerization initiator | t-butyl peroxide | 5 |
| Property values | Gardner viscosity | –Y |
| | Solid component (%) | 49.7 |

Production Example 4

Production of Silyl Ester Copolymer (a3-1)

Into a reaction vessel equipped with a stirrer, a condenser, a thermometer, a dropping device, a nitrogen introducing pipe and a heating/cooling jacket, 100 parts of xylene was introduced, and heating and stirring were carried out in a stream of nitrogen at a temperature condition of 85° C. With this temperature kept, from the dropping device, a mixture of 60 parts of triisopropylsilyl acrylate, 40 parts of methyl methacrylate and 0.3 part of 2,2'-azobisisobutyronitrile was dropped into the reaction vessel over 2 hours. Thereafter, stirring was carried out for 4 hours at this temperature, and then 0.4 part of 2,2'-azobisisobutyronitrile was added, and stirring was further carried out for 4 hours at this temperature, to thereby obtain a colorless and transparent reaction mixture containing a silyl ester copolymer (a3-1). Blending composition and property values of the copolymer (a3-1) or the reaction mixture containing the copolymer (a3-1) are set forth in Table 5.

TABLE 5

Production Example of silyl ester copolymer (a3)

| | Silyl ester copolymer (a3) | Production Example 4 a3-1 |
|---|---|---|
| Solvent | xylene | 100 |
| Components dropped | triisopropyl silyl acrylate | 60 |
| | methyl methacrylate | 40 |
| | 2,2'-azobisisobutyronitrile (initial stage) | 0.3 |
| | Total | 200.3 |
| Component added | 2,2'-azobisisobutyronitrile (later stage) | 0.4 |
| Property values | Solid component (%) | 51.2 |
| | Viscosity (cps/25° C.) | 408 |
| | Number-average molecular weight (Mn) | 9,735 |
| | Weight-average molecular weight (Mw) | 55,650 |

Examples 1 to 3 and Comparative Example 1

Production of Antifouling Coating Composition-1

The reaction mixture containing the crosslinked metal salt bond-containing copolymer (a2-1) obtained in Production Example 2, along with the antifouling agent (B) and other components, were homogenously mixed using a paint shaker, to thereby produce an antifouling coating composition having a blending composition as shown in Table 6 (Examples 1-3 and Comparative Example 1) (values in the table denote part(s) by weight).

Examples 4 to 52 and Comparative Examples 2 to 11

Production of Antifouling Coating Composition-2

The reaction mixture containing the crosslinked metal salt bond-containing copolymer (a1-1), (a2-1) or (a2-1), obtained in Production Examples 1 to 3, or containing the silyl ester copolymer (a3-1) obtained in Production Example 4, along with the antifouling agent (B) and other components, were homogenously mixed using a paint shaker, to thereby produce an antifouling coating composition having a blending composition as shown in Tables 8-1 to 8-6 (Examples 4-52 and Comparative Examples 2 to 11) (values in the tables denote part(s) by weight).

[Criteria for Evaluation of Static Antifouling Property Based on an Area of Adhesion of Undersea Organisms, in Examples and Comparative Examples]

Criteria for evaluation of static antifouling property based on an area of adhesion of undersea organisms are as follows.

0 point: The area of adhesion of the undersea organisms is about 100%.
1 point: The area of adhesion of the undersea organisms is about 51 to 99%.
2 points: The area of adhesion of the undersea organisms is about 31 to 50%.
3 points: The area of adhesion of the undersea organisms is about 11 to 30%.
4 points: The area of adhesion of the undersea organisms is about 1 to 10%.
5 points: The area of adhesion of the undersea organisms is about 0%.

<Experiment of Static Antifouling Property of Antifouling Coating Film [Examples 1 to 52 and Comparative Examples 1 to 11]>

A sandblasted steel plate (length 300 mm×width 100 mm×thickness 3.2 mm) was coated with an epoxy anticorrosive coating material (epoxy AC coating material, product name: "Bannoh 500", manufactured by Chugoku Marine Paints, Ltd.) so that the dried film thickness would be 150 μm, and then was further coated with an epoxy binder coating material (product name: "Bannoh 500N", manufactured by Chugoku Marine Paints, Ltd.) so that the dried film thickness would be 100 μm. Subsequently, the resultant plate was coated with the antifouling coating composition produced in the Example or Comparative Example one time so that the dried film thickness would be 100 μm, and then dried at room temperature for 7 days, to thereby prepare a test plate with an antifouling coating film. The above three coatings were each carried out under the condition of 1 day/1 coat.

The test plate prepared as described above was immersed and allowed to stand still for 8 months in Hiroshima Bay of Hiroshima Prefecture. During this period of time, the area (%) of the adhesion onto the coating film surface of undersea organisms excluding slime, was measured every two months. In accordance with the [Criteria for evaluation of static antifouling property based on an area of adhesion of undersea organisms], the static antifouling property of the antifouling coating film was evaluated. The results are set forth in Tables 7, 9-1 to 9-6.

<Experiment of Consumption Degree of Antifouling Coating Film [Examples 4 to 52 and Comparative Examples 2 to 11]>

A hard vinyl chloride plate of 50×50×1.5 mm was coated with the antifouling coating composition produced in Example or Comparative Example, using an applicator, so that a dried film thickness would be 250 μm. The coated plate was rotated at 15 knots, and the consumption degree (decrease in the film thickness) of the antifouling coating film was measured every month. The results are set forth in Tables 9-1 to 9-6. A unit of the consumption degree of the coating film in the tables is "μm".

<Experiment of Antifouling Coating Film Property [Examples 4 to 52 and Comparative Examples 2 to 11]>

A substrate which was a sandblasted steel plate coated with an anticorrosive coating film was coated with the antifouling coating composition produced in Example or Comparative Example, so that a dried film thickness would be 250 μm. Then, this was immersed in sterilized and filtered seawater for 3 months, and then dried at room temperature for 1 week. Each of the deteriorated antifouling coating films thus obtained was coated with an anticorrosive coating composition having the same composition, so that a dried film thickness would be 250 μm, and then the resultant coated plate was dried for 1 week. Then, this was immersed in sterilized and filtered seawater at 50° C. for 6 months, to observe the coating film about crack and peeling. Finding no crack and peeling was evaluated as AA; finding partial crack was evaluated as BB; finding partial peeling was evaluated as CC; and finding crack and peeling throughout the entire surface was evaluated as DD. The results are set forth in Tables 9-1 to 9-6.

TABLE 6

Antifouling coating composition-1

| | Ex. 1 | Ex. 2 | Ex. 3 | Com. Ex. 1 |
|---|---|---|---|---|
| Crosslinked metal salt bond-containing copolymer (a2-1) (solid component: 45.6%) | 100 | 100 | 100 | 100 |
| medetomidine | 0.025 | 0.05 | 0.1 | — |
| xylene | 5 | 5 | 5 | — |

TABLE 7

Result of antifouling property

| Immersion period | Ex. 1 | Ex. 2 | Ex. 3 | Com. Ex. 1 |
|---|---|---|---|---|
| 2 months | 4 | 4 | 5 | 2 |
| 4 months | 3 | 4 | 5 | 1 |
| 6 months | 2 | 3 | 5 | 0 |
| 8 months | 2 | 3 | 4 | 0 |

TABLE 8-1

Antifouling coating composition-2

| | Ex. 4 | Ex. 5 | Ex. 6 | Ex. 7 | Ex. 8 | Ex. 9 | Ex. 10 | Ex. 11 | Ex. 12 | Ex. 13 |
|---|---|---|---|---|---|---|---|---|---|---|
| Side-chain end metal salt bond-containing copolymer (a1-1) (solid component: 50.5%) | 45 | | | | | | | | | |
| Crosslinked metal salt bond-containing copolymer (a2-1) (solid component: 45.6%) | | 45 | 45 | 45 | 45 | | | | 5 | 5 |
| Crosslinked metal salt bond-containing copolymer (a2-2) (solid component: 49.7%) | | | | | | 45 | | | | |
| Silyl ester copolymer (a3-1) (solid component: 51.2%) | | | | | | | 45 | 30 | | |
| Rosin | | | | | | | | | 10 | 10 |
| Laroflex MP25** | | | | | | | | | 5 | 5 |
| Chlorinated paraffin | 2 | 2 | 2 | 2 | 2 | 2 | 2 | 2 | 2 | 2 |
| Talc | 15 | 15 | 15 | 15 | 15 | 15 | 15 | 3 | 3 | 3 |
| Zinc oxide | 10 | 10 | 10 | 10 | 15 | 10 | 10 | 3 | 3 | 3 |
| Settling barium sulfate | 3 | 3 | 3 | 3 | 3 | 3 | 3 | 3 | 3 | 3 |
| Exsiccated gypsum | 1 | 1 | 1 | 1 | 1 | 1 | 1 | 1 | 1 | 1 |
| Red iron oxide | 2 | 2 | 2 | 2 | 2 | 2 | 2 | 2 | 2 | 2 |
| Cuprous oxide | | | | | | | | 40 | 40 | 45 |
| Copper rhodanide | | | | | | | | | | |
| Bis(2-pyridinethiol-1-oxide)-zinc salt | 5 | 5 | 5 | 5 | | 5 | 5 | 5 | | |
| Bis(2-pyridinethiol-1-oxide)-copper salt | | | | | | | | | | |
| SEA-NINE 211N*** | | | | | | | | | 5 | |
| Pyridine-triphenylborane | | | | | | | | | | |
| Dichloro-N-((dimethylamino)-sulfonyl)-fluoro-N-(p-tolyl)-methanesulfeneamide | | | | | | | | | | |
| 2-(p-chlorophenyl)-3-cyano-4-bromo-5-trifluoromethylpyrrol | | | | | | | | | | |
| medetomidine | 0.1 | 0.4 | 0.1 | 0.05 | 0.05 | 0.1 | 0.1 | 0.1 | 0.1 | 0.1 |
| Oxidized Polyethylene wax (solid component: 20%) | 2 | 2 | 2 | 2 | 2 | 2 | 2 | 2 | 2 | 2 |
| Fatty acid amide wax (solid component: 20%) | 3 | 3 | 3 | 3 | 3 | 3 | 3 | 3 | 3 | 3 |
| Xylene | 8.9 | 8.6 | 8.9 | 8.95 | 8.95 | 8.9 | 8.9 | 2.9 | 12.9 | 12.9 |
| Propylene glycol monomethyl ether | 3 | 3 | 3 | 3 | 3 | 3 | 3 | 3 | 3 | 3 |
| Total part by weight | 100 | 100 | 100 | 100 | 100 | 100 | 100 | 100 | 100 | 100 |

**Laroflex MP25 (BASF Japan Ltd.)
***SEA-NINE 211 (Rohm and Hass, 4,5-dichloro-2-n-octyl-4-isothiazoline-3-one)

TABLE 8-2

Antifouling coating composition-2

| | Ex. 14 | Ex. 15 | Ex. 16 | Ex. 17 | Ex. 18 | Ex. 19 | Ex. 20 | Ex. 21 | Ex. 22 | Ex. 23 |
|---|---|---|---|---|---|---|---|---|---|---|
| Side-chain end metal salt bond-containing copolymer (a1-1) (solid component: 50.5%) | | | | | | | | | | |
| Crosslinked metal salt bond-containing copolymer (a2-1) (solid component: 45.6%) | 45 | 45 | 45 | 45 | 45 | 45 | 45 | 45 | 45 | 45 |
| Crosslinked metal salt bond-containing copolymer (a2-2) (solid component: 49.7%) | | | | | | | | | | |
| Silyl ester copolymer (a3-1) (solid component: 51.2%) | | | | | | | | | | |
| Rosin | | | | | | | | | | |
| Laroflex MP25 | | | | | | | | | | |
| Chlorinated paraffin | 2 | 2 | 2 | 2 | 2 | 2 | 2 | 2 | 2 | 2 |
| Talc | 10 | 10 | 10 | 10 | 10 | 10 | 10 | 10 | 10 | 10 |
| Zinc oxide | 10 | 10 | 10 | 10 | 10 | 10 | 10 | 10 | 10 | 10 |
| Settling barium sulfate | 3 | 3 | 3 | 3 | 3 | 3 | 3 | 3 | 3 | 3 |
| Exsiccated gypsum | 1 | 1 | 1 | 1 | 1 | 1 | 1 | 1 | 1 | 1 |
| Red iron oxide | 2 | 2 | 2 | 2 | 2 | 2 | 2 | 2 | 2 | 2 |
| Cuprous oxide | | | | | | | | | | |
| Copper rhodanide | | | | | | | | | | |

TABLE 8-2-continued

| | Antifouling coating composition-2 | | | | | | | | | |
|---|---|---|---|---|---|---|---|---|---|---|
| | Ex. 14 | Ex. 15 | Ex. 16 | Ex. 17 | Ex. 18 | Ex. 19 | Ex. 20 | Ex. 21 | Ex. 22 | Ex. 23 |
| Bis(2-pyridinethiol-1-oxide)zinc salt | 10 | | | | | | 5 | 5 | 5 | 5 |
| Bis(2-pyridinethiol-1-oxide)copper salt | | 10 | | | | | | | | |
| SEA-NINE 211N | | | 10 | | | | 5 | | | |
| Pyridine-triphenylborane | | | | 10 | | | | 5 | | |
| Dichloro-N-((dimethylamino)sulfonyl)-fluoro-N-(p-tolyl)methanesulfeneamide | | | | | 10 | | | | 5 | |
| 2-(p-chlorophenyl)-3-cyano-4-bromo-5-trifluoromethylpyrrol | | | | | | 10 | | | | 5 |
| medetomidine | 0.1 | 0.1 | 0.1 | 0.1 | 0.1 | 0.1 | 0.1 | 0.1 | 0.1 | 0.1 |
| Oxidized Polyethylene wax (solid component: 20%) | 2 | 2 | 2 | 2 | 2 | 2 | 2 | 2 | 2 | 2 |
| Fatty acid amide wax (solid component: 20%) | 3 | 3 | 3 | 3 | 3 | 3 | 3 | 3 | 3 | 3 |
| Xylene | 8.9 | 8.9 | 8.9 | 8.9 | 8.9 | 8.9 | 8.9 | 8.9 | 8.9 | 8.9 |
| Propylene glycol monomethyl ether | 3 | 3 | 3 | 3 | 3 | 3 | 3 | 3 | 3 | 3 |
| Total part by weight | 100 | 100 | 100 | 100 | 100 | 100 | 100 | 100 | 100 | 100 |

TABLE 8-3

| | Antifouling coating composition-2 | | | | | | | | |
|---|---|---|---|---|---|---|---|---|---|
| | Ex. 24 | Ex. 25 | Ex. 26 | Ex. 27 | Ex. 28 | Ex. 29 | Ex. 30 | Ex. 31 | Ex. 32 |
| Side-chain end metal salt bond-containing copolymer (a1-1) (solid component: 50.5%) | | | | | | | | | |
| Crosslinked metal salt bond-containing copolymer (a2-1) (solid component: 45.6%) | 45 | 45 | 45 | 45 | 45 | 45 | 30 | 30 | 30 |
| Crosslinked metal salt bond-containing copolymer (a2-2) (solid component: 49.7%) | | | | | | | | | |
| Silyl ester copolymer (a3-1) (solid component: 51.2%) | | | | | | | | | |
| Rosin | | | | | | | | | |
| Laroflex MP25 | | | | | | | | | |
| Chlorinated paraffin | 2 | 2 | 2 | 2 | 2 | 2 | 2 | 2 | 2 |
| Talc | 10 | 10 | 10 | 10 | 10 | 10 | 3 | 3 | 3 |
| Zinc oxide | 10 | 10 | 10 | 10 | 10 | 10 | 3 | 3 | 3 |
| Settling barium sulfate | 3 | 3 | 3 | 3 | 3 | 3 | 3 | 3 | 3 |
| Exsiccated gypsum | 1 | 1 | 1 | 1 | 1 | 1 | 1 | 1 | 1 |
| Red iron oxide | 2 | 2 | 2 | 2 | 2 | 2 | 2 | 2 | 2 |
| Cuprous oxide | | | | | | | 40 | 45 | |
| Copper rhodanide | | | | | | | | | 40 |
| Bis(2-pyridinethiol-1-oxide)zinc salt | | | | | | | 5 | | 5 |
| Bis(2-pyridinethiol-1-oxide)copper salt | | | | | | | | | |
| SEA-NINE 211N | 5 | 5 | 5 | | | | | | |
| Pyridine-triphenylborane | 5 | | | 5 | 5 | | | | |
| Dichloro-N-((dimethylamino)sulfonyl)-fluoro-N-(p-tolyl)methanesulfeneamide | | 5 | | 5 | | 5 | | | |
| 2-(p-chlorophenyl)-3-cyano-4-bromo-5-trifluoromethylpyrrol | | | 5 | | 5 | 5 | | | |
| medetomidine | 0.1 | 0.1 | 0.1 | 0.1 | 0.1 | 0.1 | 0.1 | 0.1 | 0.1 |
| Oxidized Polyethylene wax (solid component: 20%) | 2 | 2 | 2 | 2 | 2 | 2 | 2 | 2 | 2 |
| Fatty acid amide wax (solid component: 20%) | 3 | 3 | 3 | 3 | 3 | 3 | 3 | 3 | 3 |
| Xylene | 8.9 | 8.9 | 8.9 | 8.9 | 8.9 | 8.9 | 2.9 | 2.9 | 2.9 |
| Propylene glycol monomethyl ether | 3 | 3 | 3 | 3 | 3 | 3 | 3 | 3 | 3 |
| Total part by weight | 100 | 100 | 100 | 100 | 100 | 100 | 100 | 100 | 100 |

TABLE 8-4

| Antifouling coating composition-2 | Ex. 33 | Ex. 34 | Ex. 35 | Ex. 36 | Ex. 37 | Ex. 38 | Ex. 39 | Ex. 40 | Ex. 41 | Ex. 42 |
|---|---|---|---|---|---|---|---|---|---|---|
| Side-chain end metal salt bond-containing copolymer (a1-1) (solid component: 50.5%) | | | | | | | | | | |
| Crosslinked metal salt bond-containing copolymer (a2-1) (solid component: 45.6%) | 45 | 45 | 45 | 45 | 45 | 45 | 45 | 45 | 45 | 45 |
| Crosslinked metal salt bond-containing copolymer (a2-2) (solid component: 49.7%) | | | | | | | | | | |
| Silyl ester copolymer (a3-1) (solid component: 51.2%) | | | | | | | | | | |
| Rosin | | | | | | | | | | |
| Laroflex MP25 | | | | | | | | | | |
| Chlorinated paraffin | 2 | 2 | 2 | 2 | 2 | 2 | 2 | 2 | 2 | 2 |
| Talc | 10 | 10 | 10 | 10 | 10 | 10 | 10 | 10 | 10 | 10 |
| Zinc oxide | 10 | 10 | 10 | 10 | 10 | 10 | 10 | 10 | 10 | 10 |
| Settling barium sulfate | 10 | 10 | 10 | 10 | 10 | 10 | 9 | 9 | 9 | 9 |
| Exsiccated gypsum | 1 | 1 | 1 | 1 | 1 | 1 | 1 | 1 | 1 | 1 |
| Red iron oxide | 2 | 2 | 2 | 2 | 2 | 2 | 2 | 2 | 2 | 2 |
| Cuprous oxide | | | | | | | | | | |
| Copper rhodanide | | | | | | | | | | |
| Bis(2-pyridinethiol-1-oxide)zinc salt | 3 | | | | | | 2 | 2 | 2 | 2 |
| Bis(2-pyridinethiol-1-oxide)copper salt | | 3 | | | | | | | | |
| SEA-NINE 211N | | | 3 | | | | 2 | | | |
| Pyridine-triphenylborane | | | | 3 | | | | 2 | | |
| Dichloro-N-((dimethylamino)sulfonyl)fluoro-N-(p-tolyl)methanesulfeneamide | | | | | 3 | | | | 2 | |
| 2-(p-chlorophenyl)-3-cyano-4-bromo-5-trifluoromethylpyrrol | | | | | | 3 | | | | 2 |
| medetomidine | 0.1 | 0.1 | 0.1 | 0.1 | 0.1 | 0.1 | 0.1 | 0.1 | 0.1 | 0.1 |
| Oxidized Polyethylene wax (solid component: 20%) | 2 | 2 | 2 | 2 | 2 | 2 | 2 | 2 | 2 | 2 |
| Fatty acid amide wax (solid component: 20%) | 3 | 3 | 3 | 3 | 3 | 3 | 3 | 3 | 3 | 3 |
| Xylene | 8.9 | 8.9 | 8.9 | 8.9 | 8.9 | 8.9 | 8.9 | 8.9 | 8.9 | 8.9 |
| Propylene glycol monomethyl ether | 3 | 3 | 3 | 3 | 3 | 3 | 3 | 3 | 3 | 3 |
| Total part by weight | 100 | 100 | 100 | 100 | 100 | 100 | 100 | 100 | 100 | 100 |

TABLE 8-5

| Antifouling coating composition-2 | Ex. 43 | Ex. 44 | Ex. 45 | Ex. 46 | Ex. 47 | Ex. 48 | Ex. 49 | Ex. 50 | Ex. 51 | Ex. 52 |
|---|---|---|---|---|---|---|---|---|---|---|
| Side-chain end metal salt bond-containing copolymer (a1-1) (solid component: 50.5%) | | | | | | | | | | |
| Crosslinked metal salt bond-containing copolymer (a2-1) (solid component: 45.6%) | 45 | 45 | 45 | 45 | 45 | 45 | 30 | 30 | 30 | 45 |
| Crosslinked metal salt bond-containing copolymer (a2-2) (solid component: 49.7%) | | | | | | | | | | |
| Silyl ester copolymer (a3-1) (solid component: 51.2%) | | | | | | | | | | |
| Rosin | | | | | | | | | | |
| Laroflex MP25 | | | | | | | | | | |
| Chlorinated paraffin | 2 | 2 | 2 | 2 | 2 | 2 | 2 | 2 | 2 | 2 |
| Talc | 10 | 10 | 10 | 10 | 10 | 10 | 10 | 10 | 10 | 15 |
| Zinc oxide | 10 | 10 | 10 | 10 | 10 | 10 | 10 | 10 | 10 | 15 |
| Settling barium sulfate | 9 | 9 | 9 | 9 | 9 | 9 | 10 | 10 | 10 | 3 |
| Exsiccated gypsum | 1 | 1 | 1 | 1 | 1 | 1 | 1 | 1 | 1 | 1 |
| Red iron oxide | 2 | 2 | 2 | 2 | 2 | 2 | 2 | 2 | 2 | 2 |
| Cuprous oxide | | | | | | | 20 | 20 | | |
| Copper rhodanide | | | | | | | | | 20 | |
| Bis(2-pyridinethiol-1-oxide)zinc salt | | | | | | | 1 | | 1 | |
| Bis(2-pyridinethiol-1-oxide)copper salt | | | | | | | | | | |
| SEA-NINE 211N | 2 | 2 | 2 | | | | | | | |
| Pyridine-triphenylborane | 2 | | | 2 | 2 | | | | | |
| Dichloro-N-((dimethylamino)sulfonyl)fluoro-N-(p-tolyl)methanesulfeneamide | | 2 | | 2 | | 2 | | | | |
| 2-(p-chlorophenyl)-3-cyano-4-bromo-5-trifluoromethylpyrrol | | | 2 | | 2 | 2 | | | | |
| medetomidine | 0.1 | 0.1 | 0.1 | 0.1 | 0.1 | 0.1 | 0.1 | 0.1 | 0.1 | 0.1 |
| Oxidized Polyethylene wax (solid component: 20%) | 2 | 2 | 2 | 2 | 2 | 2 | 2 | 2 | 2 | 2 |
| Fatty acid amide wax (solid component: 20%) | 3 | 3 | 3 | 3 | 3 | 3 | 3 | 3 | 3 | 3 |
| Xylene | 8.9 | 8.9 | 8.9 | 8.9 | 8.9 | 8.9 | 5.9 | 6.9 | 5.9 | 8.9 |
| Propylene glycol monomethyl ether | 3 | 3 | 3 | 3 | 3 | 3 | 3 | 3 | 3 | 3 |
| Total part by weight | 100 | 100 | 100 | 100 | 100 | 100 | 100 | 100 | 100 | 100 |

TABLE 8-6

Antifouling coating composition-2

| | Com. Ex. 2 | Com. Ex. 3 | Com. Ex. 4 | Com. Ex. 5 | Com. Ex. 6 | Com. Ex. 7 | Com. Ex. 8 | Com. Ex. 9 | Com. Ex. 10 | Com. Ex. 11 |
|---|---|---|---|---|---|---|---|---|---|---|
| Side-chain end metal salt bond-containing copolymer (a1-1) (solid component: 50.5%) | 45 | | | | | | | | | |
| Crosslinked metal salt bond-containing copolymer (a2-1) (solid component: 45.6%) | | | 45 | | 45 | | | 5 | 5 | |
| Crosslinked metal salt bond-containing copolymer (a2-2) (solid component: 49.7%) | | 45 | | | | | | | | |
| Silyl ester copolymer (a3-1) (solid component: 51.2%) | | | | 45 | | | 30 | | | |
| Rosin | | | | | | | | 10 | 10 | |
| Laroflex MP25 | | | | | | | | 5 | 5 | |
| Paraloid B-66 (100%) resin* | | | | | | 20.7 | | | | 20.7 |
| Chlorinated paraffin | 2 | 2 | 2 | 2 | 2 | 2 | 2 | 2 | 2 | 2 |
| Talc | 15 | 15 | 15 | 15 | 15 | 15 | 3 | 3 | 3 | 15 |
| Zinc oxide | 10 | 10 | 10 | 10 | 15 | 15 | 3 | 3 | 3 | 15 |
| Settling barium sulfate | 3 | 3 | 3 | 3 | 3 | 3 | 3 | 3 | 3 | 3 |
| Exsiccated gypsum | 1 | 1 | 1 | 1 | 1 | 1 | 1 | 1 | 1 | 1 |
| Red iron oxide | 2 | 2 | 2 | 2 | 2 | 2 | 2 | 2 | 2 | 2 |
| Cuprous oxide | | | | | | | | 45 | 40 | 45 |
| Copper rhodanide | | | | | | | | | | |
| Bis(2-pyridinethiol-1-oxide)zinc salt | 5 | 5 | 5 | 5 | | | | | | |
| Bis(2-pyridinethiol-1-oxide)copper salt | | | | | | | | | | |
| SEA-NINE 211N | | | | | | | 5 | | 5 | |
| Pyridine-triphenylborane | | | | | | | | | | |
| Dichloro-N-((dimethylamino)sulfonyl)fluoro-N-(p-tolyl)-methanesulfeneamide | | | | | | | | | | |
| 2-(p-chlorophenyl)-3-cyano-4-bromo-5-trifluoromethylpyrrol | | | | | | | | | | |
| medetomidine | | | | | | | 0.1 | | | 0.1 |
| Oxidized Polyethylene wax (solid component: 20%) | 2 | 2 | 2 | 2 | 2 | 2 | 2 | 2 | 2 | 2 |
| Fatty acid amide wax (solid component: 20%) | 3 | 3 | 3 | 3 | 3 | 3 | 3 | 3 | 3 | 3 |
| Xylene | 9 | 9 | 9 | 9 | 9 | 28.2 | 3 | 13 | 13 | 33.2 |
| Propylene glycol monomethyl ether | 3 | 3 | 3 | 3 | 3 | 3 | 3 | 3 | 3 | 3 |
| Total part by weight | 100 | 100 | 100 | 100 | 100 | 100 | 100 | 100 | 100 | 100 |

*Paraloid B-66 (MMA/BMA = 50/50; 100%) resin (Rohm and Hass)

TABLE 9-1

Results of antifouling property-2

| | Ex. 4 | Ex. 5 | Ex. 6 | Ex. 7 | Ex. 8 | Ex. 9 | Ex. 10 | Ex. 11 | Ex. 12 | Ex. 13 |
|---|---|---|---|---|---|---|---|---|---|---|
| Static antifouling property/out of 5 points (immersion in seawater for 2 months) | 5 | 5 | 5 | 5 | 5 | 5 | 5 | 5 | 5 | 5 |
| Static antifouling property/out of 5 points (immersion in seawater for 4 months) | 5 | 5 | 5 | 5 | 4 | 5 | 5 | 5 | 5 | 5 |
| Static antifouling property/out of 5 points (immersion in seawater for 6 months) | 5 | 5 | 5 | 5 | 3 | 5 | 5 | 5 | 5 | 5 |
| Static antifouling property/out of 5 points (immersion in seawater for 8 months) | 5 | 5 | 5 | 5 | 3 | 5 | 5 | 5 | 5 | 5 |
| Consumption degree of coating film 3 months | 30.7 | 34.2 | 34.5 | 34.5 | 33.2 | 32.1 | 32.2 | 35.2 | 29.3 | 28.7 |
| Consumption degree of coating film 6 months | 65.2 | 72.3 | 73.2 | 72.9 | 60.1 | 67.6 | 68.2 | 74.1 | 53.3 | 54.4 |
| Ratio of consumption degree of coating film (6 months/3 months) | 2.124 | 2.114 | 2.122 | 2.113 | 1.810 | 2.106 | 2.118 | 2.105 | 1.819 | 1.895 |
| Property experiment | AA | AA | AA | AA | AA | AA | AA | AA | AA | AA |

TABLE 9-2

Results of antifouling property-2

| | Ex. 14 | Ex. 15 | Ex. 16 | Ex. 17 | Ex. 18 | Ex. 19 | Ex. 20 | Ex. 21 | Ex. 22 | Ex. 23 |
|---|---|---|---|---|---|---|---|---|---|---|
| Static antifouling property/out of 5 points (immersion in seawater for 2 months) | 5 | 5 | 5 | 5 | 5 | 5 | 5 | 5 | 5 | 5 |
| Static antifouling property/out of 5 points (immersion in seawater for 4 months) | 5 | 5 | 5 | 5 | 5 | 5 | 5 | 5 | 5 | 5 |
| Static antifouling property/out of 5 points (immersion in seawater for 6 months) | 5 | 5 | 5 | 5 | 5 | 5 | 5 | 5 | 5 | 5 |
| Static antifouling property/out of 5 points (immersion in seawater for 8 months) | 5 | 5 | 5 | 5 | 5 | 5 | 5 | 5 | 5 | 5 |
| Consumption degree of coating film 3 months | 33.6 | 33.9 | 31.2 | 31.5 | 33.5 | 33.3 | 34.7 | 32.9 | 33.5 | 34.5 |
| Consumption degree of coating film 6 months | 73.5 | 72.5 | 56.4 | 58.0 | 62.1 | 63.1 | 73.0 | 69.2 | 70.7 | 78.1 |

TABLE 9-2-continued

| Results of antifouling property-2 | | | | | | | | | | |
|---|---|---|---|---|---|---|---|---|---|---|
| | Ex. 14 | Ex. 15 | Ex. 16 | Ex. 17 | Ex. 18 | Ex. 19 | Ex. 20 | Ex. 21 | Ex. 22 | Ex. 23 |
| Ratio of consumption degree of coating film (6 months/3 months) | 2.188 | 2.139 | 1.808 | 1.841 | 1.854 | 1.895 | 2.104 | 2.103 | 2.110 | 2.264 |
| Property experiment | AA | AA | AA | AA | AA | AA | AA | AA | AA | AA |

TABLE 9-3

| Results of antifouling property-2 | | | | | | | | | |
|---|---|---|---|---|---|---|---|---|---|
| | Ex. 24 | Ex. 25 | Ex. 26 | Ex. 27 | Ex. 28 | Ex. 29 | Ex. 30 | Ex. 31 | Ex. 32 |
| Static antifouling property/out of 5 points (immersion in seawater for 2 months) | 5 | 5 | 5 | 5 | 5 | 5 | 5 | 5 | 5 |
| Static antifouling property/out of 5 points (immersion in seawater for 4 months) | 5 | 5 | 5 | 5 | 5 | 5 | 5 | 5 | 5 |
| Static antifouling property/out of 5 points (immersion in seawater for 6 months) | 5 | 5 | 5 | 5 | 5 | 5 | 5 | 5 | 5 |
| Static antifouling property/out of 5 points (immersion in seawater for 8 months) | 5 | 5 | 5 | 5 | 5 | 5 | 5 | 5 | 5 |
| Consumption degree of coating film 3 months | 30.1 | 30.9 | 32.1 | 32.0 | 33.8 | 33.5 | 34.5 | 30.1 | 32.1 |
| Consumption degree of coating film 6 months | 54.5 | 56.3 | 59.5 | 58.0 | 62.7 | 62.4 | 72.8 | 54.3 | 68.3 |
| Ratio of consumption degree of coating film (6 months/3 months) | 1.811 | 1.822 | 1.854 | 1.813 | 1.855 | 1.863 | 2.110 | 1.804 | 2.128 |
| Property experiment | AA | AA | AA | AA | AA | AA | AA | AA | AA |

TABLE 9-4

| Results of antifouling property-2 | | | | | | | | | | |
|---|---|---|---|---|---|---|---|---|---|---|
| | Ex. 33 | Ex. 34 | Ex. 35 | Ex. 36 | Ex. 37 | Ex. 38 | Ex. 39 | Ex. 40 | Ex. 41 | Ex. 42 |
| Static antifouling property/out of 5 points (immersion in seawater for 2 months) | 5 | 5 | 5 | 5 | 5 | 5 | 5 | 5 | 5 | 5 |
| Static antifouling property/out of 5 points (immersion in seawater for 4 months) | 5 | 5 | 5 | 5 | 5 | 5 | 5 | 5 | 5 | 5 |
| Static antifouling property/out of 5 points (immersion in seawater for 6 months) | 5 | 5 | 5 | 5 | 5 | 5 | 5 | 5 | 5 | 5 |
| Static antifouling property/out of 5 points (immersion in seawater for 8 months) | 5 | 5 | 5 | 5 | 5 | 5 | 5 | 5 | 5 | 5 |
| Consumption degree of coating film 3 months | 33.2 | 33.1 | 31.2 | 32.6 | 32.3 | 33.1 | 32.1 | 33.2 | 32.9 | 34.7 |
| Consumption degree of coating film 6 months | 71.7 | 71.2 | 56.5 | 59.8 | 59.5 | 62.5 | 67.5 | 69.9 | 69.2 | 77.2 |
| Ratio of consumption degree of coating film (6 months/3 months) | 2.160 | 2.151 | 1.811 | 1.834 | 1.842 | 1.888 | 2.103 | 2.105 | 2.103 | 2.225 |
| Property experiment | AA | AA | AA | AA | AA | AA | AA | AA | AA | AA |

TABLE 9-5

| Results of antifouling property-2 | | | | | | | | | | |
|---|---|---|---|---|---|---|---|---|---|---|
| | Ex. 43 | Ex. 44 | Ex. 45 | Ex. 46 | Ex. 47 | Ex. 48 | Ex. 49 | Ex. 50 | Ex. 51 | Ex. 52 |
| Static antifouling property/out of 5 points (immersion in seawater for 2 months) | 5 | 5 | 5 | 5 | 5 | 5 | 5 | 5 | 5 | 5 |
| Static antifouling property/out of 5 points (immersion in seawater for 4 months) | 5 | 5 | 5 | 5 | 5 | 5 | 5 | 5 | 5 | 4 |
| Static antifouling property/out of 5 points (immersion in seawater for 6 months) | 5 | 5 | 5 | 5 | 5 | 5 | 5 | 5 | 5 | 3 |
| Static antifouling property/out of 5 points (immersion in seawater for 8 months) | 5 | 5 | 5 | 5 | 5 | 5 | 5 | 5 | 5 | 3 |
| Consumption degree of coating film 3 months | 32.5 | 32.6 | 33.4 | 32.1 | 34.7 | 33.5 | 35.1 | 31.8 | 33.0 | 33.8 |
| Consumption degree of coating film 6 months | 58.9 | 59.3 | 60.6 | 58.2 | 63.5 | 62.1 | 73.9 | 57.3 | 69.4 | 61.8 |
| Ratio of consumption degree of coating film (6 months/3 months) | 1.812 | 1.819 | 1.814 | 1.813 | 1.830 | 1.854 | 2.105 | 1.802 | 2.103 | 1.828 |
| Property experiment | AA | AA | AA | AA | AA | AA | AA | AA | AA | AA |

TABLE 9-6

Results of antifouling property-2

| | Com. Ex. 2 | Com. Ex. 3 | Com. Ex. 4 | Com. Ex. 5 | Com. Ex. 6 | Com. Ex. 7 | Com. Ex. 8 | Com. Ex. 9 | Com. Ex. 10 | Com. Ex. 11 |
|---|---|---|---|---|---|---|---|---|---|---|
| Static antifouling property/out of 5 points (immersion in seawater for 2 months) | 2 | 2 | 2 | 2 | 1 | 3 | 3 | 4 | 2 | 2 |
| Static antifouling property/out of 5 points (immersion in seawater for 4 months) | 1 | 1 | 2 | 1 | 1 | 0 | 3 | 3 | 2 | 1 |
| Static antifouling property/out of 5 points (immersion in seawater for 6 months) | 1 | 1 | 1 | 1 | 0 | 0 | 2 | 2 | 1 | 0 |
| Static antifouling property/out of 5 points (immersion in seawater for 8 months) | 1 | 1 | 1 | 1 | 0 | 0 | 1 | 2 | 1 | 0 |
| Consumption degree of coating film 3 months | 29.4 | 31.0 | 32.3 | 29.9 | 29.3 | 5.8 | 29.5 | 27.2 | 26.9 | 3.9 |
| Consumption degree of coating film 6 months | 51.3 | 55.1 | 56.3 | 53.7 | 51.9 | 6.6 | 51.6 | 47.4 | 46.3 | 4.3 |
| Ratio of consumption degree of coating film (6 months/3 months) | 1.745 | 1.777 | 1.743 | 1.796 | 1.771 | 1.138 | 1.749 | 1.743 | 1.721 | 1.103 |
| Property experiment | AA | AA | AA | AA | AA | CC | AA | AA | AA | CC |

The invention claimed is:

1. An antifouling coating composition, comprising a hydrolyzable copolymer (A) and an antifouling agent (B), wherein:
the hydrolyzable copolymer (A) is at least one hydrolyzable copolymer selected from the group consisting of:
(a1) a metal salt bond-containing copolymer which is an acrylic resin or a polyester resin and has a side-chain end group represented by formula (I):

$$-COO-M-O-COR^1 \qquad (I),$$

where M is zinc or copper, and $R^1$ is an organic group;
(a2) a metal salt bond-containing copolymer having a component unit derived from a monomer (a21) represented by formula (II):

$$CH_2=C(R^2)-COO-M-O-CO-C(R^2)=CH_2$$

where M is zinc or copper, and $R^2$ is a hydrogen atom or a methyl group, and
a component unit derived from an unsaturated monomer (a22) copolymerizable with the monomer (a21) and comprising at least one unsaturated monomer selected from the group consisting of an alkyl(meth)acrylate, an alkoxyalkyl(meth)acrylate, a hydroxyalkyl(meth)acrylate, and a monobasic acid metal (meth)acrylate represented by formula (IV):

$$CH_2=C(R^2)-COO-M-O-COR^1 \qquad (IV),$$

where M is zinc or copper, $R^1$ is an organic group, and $R^2$ is a hydrogen atom or a methyl group; and
(a3) a silyl ester copolymer having
a component unit derived from a monomer (a31) represented by formula (III):

$$R^7-CH=C(R^3)-COO-SiR^4R^5R^6 \qquad (III),$$

where
$R^3$ is a hydrogen atom or a methyl group,
$R^4$, $R^5$ and $R^6$ are each independently a hydrocarbon group,
$R^7$ is a hydrogen atom or $R^8-O-CO-$,
$R^8$ is an organic group or a silyl group represented by $-SiR^9R^{10}R^{11}$, and
$R^9$, $R^{10}$ and $R^{11}$ are each independently a hydrocarbon group, and optionally
a component unit derived from an unsaturated monomer (a32) copolymerizable with the monomer (a31) and comprising at least one unsaturated monomer selected from the group consisting of an alkyl(meth)acrylate, an alkoxyalkyl(meth)acrylate, and a hydroxyalkyl(meth)acrylate;

the antifouling agent (B) comprises medetomidine; and the composition has superior antifouling properties as compared with a composition of either the hydrolyzable copolymer (A) or the antifouling agent (B) alone.

2. The antifouling coating composition according to claim 1, comprising 0.01 to 200 parts by weight of medetomidine based on 100 parts by weight of the hydrolyzable copolymer (A).

3. The antifouling coating composition according to claim 1, wherein the antifouling agent (B) further comprises at least one antifouling agent selected from the group consisting of cuprous oxide, copper rhodanide, copper pyrithione, zinc pyrithione, 4,5-dichloro-2-n-octyl-4-isothiazoline-3-one, triphenylboron.amine complex, dichloro-N-((dimethylamino)sulfonyl)fluoro-N-(p-tolyl)methanesulfeneamide, 2-(p-chlorophenyl)-3-cyano-4-bromo-5-trifluoromethylpyrrol, copper, N,N-dimethyldichlorophenyl urea, 2,4,6-trichlorophenyl maleimide, 2-methylthio-4-tert-butylamino-6-cyclopropyl-S-triazine, 2,4,5,6-tetrachloroisophthalonitrile, bisdimethyldithiocarbamoyl zinc ethylene bisdithiocarbamate, chloromethyl-n-octyldisulfide, N,N'-dimethyl-N'-phenyl-(N-fluorodichloromethylthio)sulfamide, tetraalkyl thiuram disulfide, zinc dimethyldithio carbamate, zinc ethylene bisdithio carbamate, 2,3-dichloro-N-(2',6'-diethylphenyl) maleimide, and 2,3-dichloro-N-(2'-ethyl-6'-methylphenyl) maleimide.

4. The antifouling coating composition according to claim 1, wherein the metal salt bond-containing copolymer (a1) is a copolymer of two or more kinds of monobasic acid metal (meth)acrylates each represented by formula (IV):

$$CH_2=C(R^2)-COO-M-O-COR^1 \qquad (IV),$$

where M is zinc or copper, $R^1$ is an organic group, and $R^2$ is a hydrogen atom or a methyl group.

5. The antifouling coating composition according to claim 4, wherein the organic group $R^1$ of the monobasic acid metal (meth)acrylate represented by the formula (IV) is an organic acid residue formed from a monobasic acid, and the organic acid residue is a saturated or unsaturated aliphatic hydrocarbon group having 2 to 30 carbon atoms, a saturated or unsaturated alicyclic hydrocarbon group having 3 to 20 carbon atoms, an aromatic hydrocarbon group having 6 to 18 carbon atoms, or a substituted group thereof.

6. The antifouling coating composition according to claim 1, wherein the metal salt bond-containing copolymer (a1) is a copolymer comprising:
a component unit derived from a monobasic acid metal (meth)acrylate represented by formula (IV):

$$CH_2=C(R^2)-COO-M-O-COR^1 \qquad (IV),$$

where M is zinc or copper, $R^1$ is an organic group, and $R^2$ is a hydrogen atom or a methyl group; and a component unit derived from at least one unsaturated monomer selected from the group consisting of an alkyl (meth)acrylate, an alkoxyalkyl(meth)acrylate and a hydroxyalkyl(meth)acrylate.

7. The antifouling coating composition according to claim 1, wherein, in the metal salt bond-containing copolymer (a1), the side-chain end group of formula (I) comprises 0.5 to 20% by weight of zinc, copper, or both, relative to a weight of the copolymer (a1).

8. The antifouling coating composition according to claim 1, wherein the monomer (a21) comprises at least one monomer selected from the group consisting of zinc diacrylate, zinc dimethacrylate, copper diacrylate and copper dimethacrylate.

9. The antifouling coating composition according to claim 1, wherein the unsaturated monomer (a22) comprises the monobasic acid metal (meth)acrylate represented by formula (IV) and at least one unsaturated monomer selected from the group consisting of an alkyl(meth)acrylate, an alkoxyalkyl (meth)acrylate and a hydroxyalkyl(meth)acrylate.

10. The antifouling coating composition according to claim 1, wherein, in the metal salt bond-containing copolymer (a2), the component unit derived from the monomer (a21) comprises 0.5 to 20% by weight of zinc, copper, or both, relative to a weight of the copolymer (a2).

11. The antifouling coating composition according to claim 1, wherein the organic group $R^1$ in the metal salt bond-containing copolymer (a1) is an organic acid residue formed from a monobasic acid, and the organic acid residue is a saturated or unsaturated aliphatic hydrocarbon group having 2 to 30 carbon atoms, a saturated or unsaturated alicyclic hydrocarbon group having 3 to 20 carbon atoms, an aromatic hydrocarbon group having 6 to 18 carbon atoms, or a substituted group thereof.

12. The antifouling coating composition according to claim 1, wherein the monomer (a31) comprises a trialkylsilyl (meth)acrylate.

13. An antifouling coating film formed from the antifouling coating composition according to claim 1.

14. A substrate, comprising a coating film in which a surface of the substrate is coated with the coating film obtained by curing the antifouling coating composition according to claim 1, where the substrate is one in contact with seawater or fresh water.

15. A method for producing a substrate with a coating film, the method comprising applying or impregnating the antifouling coating composition according to claim 1 to a surface of a substrate, and curing the composition to form the coating film, where the substrate is one in contact with seawater or fresh water.

16. The antifouling coating composition according to claim 1, wherein the antifouling agent (B) further comprises bis(2-pyridinethiol-1-oxide)copper salt or bis(2-pyridinethiol-1-oxide) zinc salt.

* * * * *